(12) United States Patent
Cerami et al.

(10) Patent No.: US 10,669,590 B2
(45) Date of Patent: Jun. 2, 2020

(54) PIK3CA FUSIONS

(71) Applicant: BLUEPRINT MEDICINES CORPORATION, Cambridge, MA (US)

(72) Inventors: Ethan G. Cerami, Winchester, MA (US); Christoph Lengauer, Cambridge, MA (US); Nicolas Stransky, Charlestown, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 0 days.

(21) Appl. No.: 16/287,438

(22) Filed: Feb. 27, 2019

(65) Prior Publication Data

US 2019/0185942 A1    Jun. 20, 2019

Related U.S. Application Data

(62) Division of application No. 15/304,656, filed as application No. PCT/US2015/026501 on Apr. 17, 2015, now abandoned.

(60) Provisional application No. 61/981,546, filed on Apr. 18, 2014.

(51) Int. Cl.
| | |
|---|---|
| *C12Q 1/68* | (2018.01) |
| *C07H 21/04* | (2006.01) |
| *C12Q 1/6886* | (2018.01) |
| *A61K 31/7088* | (2006.01) |
| *C12N 15/113* | (2010.01) |
| *C12Q 1/6806* | (2018.01) |
| *C12Q 1/6813* | (2018.01) |

(52) U.S. Cl.
CPC ........ *C12Q 1/6886* (2013.01); *A61K 31/7088* (2013.01); *C12N 15/1137* (2013.01); *C12Q 1/6806* (2013.01); *C12Q 1/6813* (2013.01); *C12Q 2600/156* (2013.01)

(58) Field of Classification Search
None
See application file for complete search history.

(56) References Cited

U.S. PATENT DOCUMENTS

2014/0315199 A1    10/2014    Rhodes

FOREIGN PATENT DOCUMENTS

| GB | 2 453 173 A | 4/2009 |
|---|---|---|
| WO | WO 2010/081001 A2 | 7/2010 |
| WO | WO 2012/068000 A2 | 5/2012 |
| WO | WO 2013/074518 A1 | 5/2013 |

OTHER PUBLICATIONS

International Patent Application No. PCT/US2015/026501, filed Apr. 17, 2015, by Blueprint Medicines Corp.: International Search Report and Written Opinion, dated Jul. 29, 2015.
Mehra, R. et al. (2014) "Primary Urethral Clear-Cell Adenocarcinoma. Comprehensive Analysis by Surgical Pathology, Cytopathology, and Next-Generation Sequencing" *Am J Pathol*, 184(3):584-591.
Scott, D.W. et al. (2012) "TBL1XR1/TP63: a novel recurrent gene fusion in B-cell non-Hodgkin Lymphoma" *Blood*, 119(21):4949-4952.
Soda, M. et al. (2007) "Identification of the transforming EML4-ALK fusion gene in non-small-cell lung cancer" *Nature*, 448:561-566.
Stransky, N. et al. (2014) "The landscape of kinase fusions in cancer" *Nature Communications*, 5:4846, and "Supplementary Data 2: List of all recurrent kinase fusions and sample ids" retrieved from URL: http://www.nature.com/ncomm/2014/140910/ncomms5846/extref/ncomms5846-s3.xlsx.

*Primary Examiner* — Jeanine A Goldberg
(74) *Attorney, Agent, or Firm* — Finnegan, Henderson, Farabow, Garrett and Dunner, LLP

(57) ABSTRACT

The invention provides PIK3CA (phosphatidylinositol-4,5-bisphosphate 3-kinase, catalytic subunit alpha) gene fusions, and fragments of those gene fusions. The invention further provides methods of diagnosing and treating diseases or disorders associated with PIK3CA fusions, such as conditions mediated by PIK3CA aberrant expression or activity, or overexpression of PIK3CA.

6 Claims, 10 Drawing Sheets

Specification includes a Sequence Listing.

FIG. 1A

```
   1  GGGGTTATAA TTGCCTCTCA CCCCCCGGAG GGGTTATTTT GGGGGTGGTT    50
  51  GGAGGCGGTG GCGGCGGCGG CGAGGAGGGG AATTTCCTTG TGCCTCCATT   100
 101  CCCGGGAGGG GGGAGCGGCG TTGGAGGCCA CCGTTCCAG/GTTTCTGCTT   150
 151  TGGGACAACC ATACATCTAA TTCCTTAAAG TAGTTTTATA TGTAAAACTT   200
 201  GCAAAGAATC AGAACAATGC CTCCACGACC ATCATCAGGT GAACTGTGGG   250
 251  GCATCCACTT GATGCCCCCA AGAATCCTAG TAGAATGTTT ACTACCAAAT   300
 301  GGAATGATAG TGACTTTAGA ATGCCTCCGT GAGGCTACAT TAATAACCAT   350
 351  AAAGCATGAA CTATTTAAAG AAGCAAGAAA ATACCCCCTC CATCAACTTC   400
 401  TTCAAGATGA ATCTTCTTAC ATTTTCGTAA GTGTTACTCA AGAAGCAGAA   450
 451  AGGGAAGAAT TTTTTGATGA AACAAGACGA CTTTGTGACC TTCGGCTTTT   500
 501  TCAACCCTTT TTAAAAGTAA TTGAACCAGT AGGCAACCGT GAAGAAAAGA   550
 551  TCCTCAATCG AGAAATTGGT TTTGCTATCG GCATGCCAGT GTGTGAATTT   600
 601  GATATGGTTA AAGATCCAGA AGTACAGGAC TTCCGAAGAA ATATTCTGAA   650
 651  CGTTTGTAAA GAAGCTGTGG ATCTTAGGGA CCTCAATTCA CCTCATAGTA   700
 701  GAGCAATGTA TGTCTATCCT CCAAATGTAG AATCTTCACC AGAATTGCCA   750
 751  AAGCACATAT ATAATAAATT AGATAAAGGG CAAATAATAG TGGTGATCTG   800
 801  GGTAATAGTT TCTCCAAATA ATGACAAGCA GAAGTATACT CTGAAAATCA   850
 851  ACCATGACTG TGTACCAGAA CAAGTAATTG CTGAAGCAAT CAGGAAAAAA   900
 901  ACTCGAAGTA TGTTGCTATC CTCTGAACAA CTAAAACTCT GTGTTTTAGA   950
 951  ATATCAGGGC AAGTATATTT TAAAAGTGTG TGGATGTGAT GAATACTTCC  1000
1001  TAGAAAAATA TCCTCTGAGT CAGTATAAGT ATATAAGAAG CTGTATAATG  1050
1051  CTTGGGAGGA TGCCCAATTT GATGTTCATG GCTAAAGAAA GCCTTATTC   1100
1101  TCAACTGCCA ATGGACTGTT TTACAATGCC ATCTTATTCC AGACGCATTT  1150
1151  CCACAGCTAC ACCATATATG AATGGAGAAA CATCTACAAA ATCCCTTTGG  1200
1201  GTTATAAATA GTGCACTCAG AATAAAAATT CTTTGTGCAA CCTACGTGAA  1250
1251  TGTAAATATT CGACACATTG ATAAGATCTA TGTTCGAACA GGTATCTACC  1300
1301  ATGGAGGAGA ACCCTTATGT GACAATGTGA ACACTCAAAG AGTACCTTGT  1350
1351  TCCAATCCCA GGTGGAATGA ATGGCTGAAT TATGATATAT ACATTCCTGA  1400
1401  TCTTCCTCGT GCTGCTCGAC TTTGCCTTTC CATTTGCTCT GTTAAAGGCC  1450
1451  GAAAGGGTGC TAAAGAGGAA CACTGTCCAT GGCATGGGG AAATATAAAC   1500
1501  TTGTTTGATT ACACAGACAC TCTAGTATCT GGAAAAATGG CTTTGAATCT  1550
1551  TTGGCCAGTA CCTCATGGAT TAGAAGATTT GCTGAACCCT ATTGGTGTTA  1600
1601  CTGGATGCAA TCCAAATAAA GAAACTCCAA GCTTAGAGTT GGAGTTTGAC  1650
1651  TGGTTCAGCA GTGTGGTAAA GTTCCCAGAT ATGTCAGTGA TTGAAGAGCA  1700
1701  TGCCAATTGG TCTGTATCCC GAGAAGCAGG ATTTAGCTAT TCCCACGCAG  1750
1751  GACTGAGTAA CAGACTAGCT AGAGACAATG AATTAAGGGA AAATGACAAA  1800
1801  GAACAGCTCA AAGCAATTTC TACACGAGAT CCTCTCTCTG AAATCACTGA  1850
1851  GCAGGAGAAA GATTTCTAT GGAGTCACAG ACACTATTGT GTAACTATCC   1900
1901  CCGAAATTCT ACCCAAATTG CTTCTGTCTG TTAAATGGAA TTCTAGAGAT  1950
1951  GAAGTAGCCC AGATGTATTC CTTGGTAAAA GATTGGCCTC CAATCAAACC  2000
2001  TGAACAGGCT ATGGAACTTC TGGACTGTAA TTACCCAGAT CCTATGGTTC  2050
2051  GAGGTTTTGC TGTTCGGTGC TTGGAAAAAT ATTTAACAGA TGACAAACTT  2100
2101  TCTCAGTATT TAATTCAGCT AGTACAGGTC CTAAAATATG AACAATATTT  2150
2151  GGATAACTTG CTTGTGAGAT TTTTACTGAA GAAAGCATTG ACTAATCAAA  2200
2201  GGATTGGCA CTTTTCTTT TGGCATTTAA AATCTGACAT GCACAATAAA    2250
2251  ACAGTTAGCC AGAGGTTTGG CCTGCTTTTG GAGTCCTATT GTCGTGCATG  2300
2301  TGGATGTAT TTGAAGCACC TGAATAGGCA AGTCGAGGCA ATGAAAAGC    2350
2351  TCATTAACTT AACTGACATT CTCAAACAGG AGAAGAAGGA TGAAACACAA  2400
2401  AAGGTACAGA TGAAGTTTTT AGTTGAGCAA ATGAGGCCAC CAGATTTCAT  2450
```

```
2451  GGATGCTCTA CAGGGCTTTC TGTCTCCTCT AAACCCTGCT CATCAACTAG  2500
2501  GAAACCTCAG GCTTGAAGAG TGTGGAATTA TGTCCTCTGC AAAAAGGCCA  2550
2551  CTGTGGTTCA ATTGCCAGAA CCCACACATC ATGTCAGAGT TACTGTTTCA  2600
2601  GAACAATGAG ATCATCTTTA AAAATGGGGA TGATTTACGG CAAGATATGT  2650
2651  TAACACTTCA AATTATTCGT ATTATGGAAA ATATCTGGCA AAATCAAGGT  2700
2701  CTTGATCTTC GAATGTTACC TTATGGTTGT CTGTCAATCG GTGACTGTGT  2750
2751  GTGACTTGTT GAGGTGGTGC GAAATTCTCA CACTATTATG CAAATTCAGT  2800
2801  GCAAAGGCGG CTTGAAGGT GCACTGCAGT TCAACAGCCA CACACTACAT  2850
```

```
2851  CAGTGGCTCA AAGACAAGAA CAAAGGAGAA ATATATGATG CAGCCATTGA  2900
2901  CCTGTTTACA CGTTCATGTG CTGGATACTG TGTAGCTACC TTCATTTTGG  2950
2951  GAATTGGAGA TCGTCACAAT AGTAACATCA TGGTGAAAGA CGATGGACAA  3000
3001  CTGTTTCATA TAGATTTTGG ACACTTTTTG GATCACAAGA AGAAAAAATT  3050
3051  TGGTTATAAA CGAGAACGTG TGCCATTTGT TTTGACACAG GATTCTTAA   3100
3101  TAGTGATTAG TAAAGGAGCC CAAGAATGCA CAAAGACAAG AGAATTTGAG  3150
3151  AGGTTTCAGG AGATGTGTTA CAAGGCTTAT CTAGCTATTC GACAGCATGC  3200
3201  CAATCTCTTC ATAAATCTTT TCTCAATGAT GCTTGGCTCT GGAATGCCAG  3250
3251  AACTACAATC TTTTGATGAC ATTGCATACA TTCAAAAGAC CCTAGCCTTA  3300
3301  GATAAAACTG AGCAAGAGGC TTTGGAGTAT TTCATGAAAC AAATGAATGA  3350
3351  TGCACATCAT GGTGGCTGGA GAACAAAAAT GGATTGGATC TTCCACACAA  3400
3401  TTAAACAGCA TGCATTGAAC TGA                               3423
                                              (SEQ ID NO:1)
```

FIG. 2

```
   1  MPPRPSSGEL WGIHLNPPRI LVECLLPNGM IVTLECLREA TLITIKHELF    50
  51  KEARKYPLHQ LLQDESSYIF VSVTQEAERE EFFDETRRLC DLRLFQPFLK   100
 101  VIEPVGNREE KILNREIGPA IGMPVCEFDM VKDPEVQDFR RNILNVCKEA   150
 151  VDLRDLNSPH SRAMYVYPPN VESSPELPKH IYNKLDKGQI IVVIWVIVSP   200
 201  NNDKQKYTLK INHDCVPEQV IAEAIRKKTR SMLLSSEQLK LCVLEYQGKY   250
 251  ILKVCGCDEY FLEKYPLSQY KYIRSCIMLG RMPNLMLMAK ESLYSQLPMD   300
 301  CFTMPSYSRR ISTATPYMNG ETSTKSLWVI NSALRIKILC ATYVNVNIRD   350
 351  IDKIYVRTGI YRGGEPLCDN VNTQRVPCSN PRWNEWLNYD IYIPDLPRAA   400
 401  RLCLSICSVK GRKGAKEEHC PLAWGNINLF DYTDTLVSGK MALNLWPVFH   450
 451  GLEDLLNPIG VTGSNPNKET PCLELEPDWF SSVVKFPDMS VIEEHANWSV   500
 501  SREAGFSYSH AGLSNRLARD NELRENDKEQ LKAISTRDPL SEITEQEKDF   550
 551  LWSHREYCVT IPEILPKLLL SVKWNSRDEV AQMYCLVKDW PPIKPEQAME   600
 601  LLDCNYPDPM VRGFAVRCLE KYLTDDKLSQ YLIQLVQVLK YEQYLDNLLV   650
 651  RFLLKKALTN QRIGHFFWH LKSEMHNKTV SQRPGLLLES VCRACGMYLK    700
 701  HLNEQVEAME KLINLTDILK QEKKDETQKV QMKFLVEQMR RPDFMDALQG   750
 751  FLSPLNPAHQ LGNLRLEECR IMSSAKRPLW LNWENPDIMS ELLFQNNEII   800
 801  FKNGDDLRQD MLTLQIIRIM ENIWQNQGLD LRMLPYGCLS IGDCVGLIEV   850
 851  VRNSHTIMQI QCKGGLKGAL QFNSHILHQW LKDKNKGEIY DAAIDLFTRS   900
 901  CAGYCVATFY LGIGDRHNSN IMVKEDGQLF HIDFGHFLDH KKKKFGYKRE   950
 951  RVPFVLTQDF LIVISKGAQE CTKTREFERF QEMCYKAYLA IRQHANLFIN  1000
1001  LFSMMLGSGM PELQSFUDIA YIRKTLALDK TEQEALEYFM KQMNDAHHGG  1050
1051  WTTKMDWIFH TIKQHALN                                    1068
                              (SEQ ID NO:2)
```

FIG. 3A

```
   1  GTGGCGGCGG CGGCTGGAGG AGGAGAGCGG CGGCGGCGGG AGCAGCGAAG    50
  51  GGGGCGGCAG GGATCCTCCA GGCTGCCGGC TGGGAAGGCG TGGGCGACCC   100
 101  GGTGTGTGGC GCGCCCAGAG CCCCGCGTTT CAGCCCTAGG GAAGGAAGCC   150
 151  AGTTGAGGGA AGTTCTCCAT GAATGTACGT CACAATGATG ATGACCGACC   200
 201  AAATCCCTCT GGAACTGCCA CCATGCTGA ATGGAGAGGT AGCCATGATG   250
 251  CCCACTGG TGAATGGAGA TGCAGCTCAG CAGGTTATTC TCGTTCAAGT   300
 301  TAATCCAGCT GAGACTTTCA CAATAAGAGC AGAGGATGGA ACACTTCAGT   350
 351  GCATTCAAG/GTTTCTGCTTT GGGACAACCA TACATCTAAT TCCTTAAAGT   400
 401  AGTTTTATAT GTAAAACTGG CAAAGAATCA GAACAATGCC TCCACGACCA   450
 451  TCATCAGCTG AACTGTGGGG CATCCACTTG ATGCCCCCAA GAATCCTAGT   500
 501  AGAATGTTTA CTACCAAATG GAATGATAGT GACTTTAGAA TGCCTCCGTG   550
 551  AGGCTACATT AATAACCATA AAGCATGAAC TATTTAAAGA AGCAAGAAAA   600
 601  TACCCCCTCC ATCAACTTCT TCAGATGAA TCTTCTTACA TTTTCGTAAG   650
 651  TGTTACTCAA GAAGCAGAAA GGGAAGAATT TTTTGATGAA ACAAGACGAC   700
 701  TTTGTGACCT TCGGCTTTTT CAACCCTTTT TAAAAGTAAT TGAACCAGTA   750
 751  GGCAACCGTG AAGAAAAGAT CCTCAATCGA GAAATTCGTT TTGCTATGCC   800
 801  CATGCCAGTG TGTGAATTCG ATATGGTTAA AGATCCAGAA GTACAGGACT   850
 851  TCCGAACAAA TATTCTGAAC GTTTGTAAAG AAGCTGTGGA TCTTAGGGAC   900
 901  CTCAATTCAC CTCATAGTAG AGCAATGTAT GTCTATCCTC CAAATGTAGA   950
 951  ATCTTCACCA GAATTGCCAA AGCACATATA TAATAAATTA GATAAAGGGC  1000
1001  AAATAATAGT GGTGATCTGG GTAATAGTTT CTCCAAATAA TGACAAGCAG  1050
1051  AAGTATACTC TGAAAATCAA CCATGACTGT GTACCAGAAC AAGTAAATGC  1100
1101  TGAAGCAATC AGGAAAAAA CTCGAAGTAT GTTGCTATCC TCTGAACAAC  1150
1151  TAAAACTCTG TGTTTTAGAA TATCAGGCA AGTATATTTT AAAAGTGTGT  1200
1201  GGATGTGATG AATACTTCCT AGAAAAATAT CCTCTGAGTC AGTATAAGTA  1250
1251  TATAAGAAGC TGTATAATGC TTGGGAGGAT GCCCAATTTG ATGTTGATGG  1300
1301  CTAAAGAAAG GCTTTATTCT CAACTGCCAA TGGACTGTTT TACAATGCCA  1350
1351  TCTTATTCCA GACGCATTC CACAGCTACA CCATATATGA ATGGAGAAAC  1400
1401  ATCTACAAAA TCCCTTTGGG TTATAAATAG TGCACTCAGA ATAAAAATTC  1450
1451  TTTGTGCAAC CTACGTGAAT GTAAATATTC GAGACATTGA TAAGATCTAT  1500
1501  GTTCCAAACG GTATCTACCA TGGAGGAGAA CCCTTATGTG ACAATGTGAA  1550
1551  CACTCAAAGA GTACCTTGTT CCAATCCTAG GTGGAATGAA TGGCTGAATT  1600
1601  ATGATATATA CATTCCTGAT CTTCCTCGTG CTGCTCGACT TTGCCTTTCC  1650
1651  ATTTGCTCTG TTAAAGGCCG AAAGGGTGCT AAAGAGGAAC ACTGTCCATT  1700
1701  GGCATGGGCA AATATAAAACT TGTTTGATTA CACAGACACT CTAGTATCTG  1750
1751  GAAAATGGC TTTGAAACTT TGGCCAGTAC CTCATGGATT AGAAGATTTG  1800
1801  CTGAACCCTA TTGGTGTTAC TGGATCAAAT CCAAATAAAG AAACTCCATG  1850
1851  CTTAGAGTTG GAGTTTGACT GGTTCAGCAG TGTGTAAAG TTCCAGATA  1900
1901  TGTCAGTGAT TGAAGAGCAT GCCAATTGGT CTGTATCCCG AGAAGTAGGA  1950
1951  TTTAGCTATT CCCACGGCAG ACTGAGTAAC AGACTAGCTA CAGACAATGA  2000
2001  ATTAAGGGAA AATGACAAAG AACAGCTCAA AGCAATTTCT ACACGAGATC  2050
2051  CTCTCTCTGA AATCACTGAG CAGGAGAAAG ATTTTCTATG GAGTCACAGA  2100
2101  CACTATTGTG TAACTATCCC CGAAATTCTA CCCAAATTGC TTCTGTCTGT  2150
2151  TAAATGGAAT TCTAGAGATG AAGTAGCCCA GATGTATTGC TTGGTAAAAG  2200
2201  ATTGGCCTCC AATCAAACCT GAACAGGCTA TGGAACTTCT GGACTGTAAT  2250
2251  TACCCAGATC CTATGTTCG AGGTTTGCT GTTCGGTCCT TGGAAAAATA  2300
2301  TTTAACAGAT GACAAACTTT CTCAGTATTT AATTCAGCTA GTACAGGTCC  2350
2351  TAAAATATGA ACAATATTTG GATAACTTGC TTGTGAGATT TTTACTGAAG  2400
```

```
2401  AAAGCATTGA  CTAATCAAAG  GATTGGGCAC  TTTTTCTGTT  GGCATTTAAA  2450
2451  ATCTGAGATG  CACAATAAAA  CAGTTAGGCA  GAGGTTGGC   CTGCTTTTGG  2500
2501  AGTGTATTG   TGTGCATGT   GGGATGTATT  TGAAGCACCT  GAATAGGCAA  2550
2551  GTCGAGGCAA  TGGAAAGCT   CATTAACTTA  ACTGACATTG  TCAAACAGGA  2600
2601  GAAGAAGGT   GAAACACAAA  AGGTACGGAT  GAAGTTTTA   GTTGAGCAAA  2650
2651  TCAGGCGACC  AGATTTCATG  GATGCTCTAC  AGGGCTTTCT  GTCTCCTCTA  2700
2701  AACCTGCTC   GTCAACTAGG  AAACCTCAGG  CTTGAAGAGT  GTCGAATTAT  2750
2751  GTCCTCTGCA  AAAAGGCCAC  TGTGGTTGAA  TTGGGACAAC  CCAGACATCA  2800
2801  TGTCAGAGTT  ACTGTTTCAG  AACAATGAGA  TCATCTTAA   AAATGGGGAT  2850
```

```
2851  GATTTACGGC AAGATATGCT AACACTTCAA ATTATTCGTA TTATGGAAAA  2900
2901  TATCTGGCAA AATCAAGGTC TTGATCTTCG AATGTTACCT TATGGTTGTC  2950
2951  TGTCAATCGG TGACTGTGTG GGACTTATTG AGGTGGTGCG AAATTCTCAC  3000
3001  ACTATTATGC AAATTCAGTG CAAAGGCGGC TTGAAAGGTG CACTGCAGTT  3050
3051  CAACAGCCAC ACACTACATC AGTGGCTCAA AGACAAGAAC AAAGGAGAAA  3100
3101  TATATGATGC AGCCATTGAC CTGTTTACAC GTTCATGTGC TGGATACTGT  3150
3151  GTAGCTACCT TCATTTTGGG AATTGAGAT CGTCACAATA GTAACATCAT  3200
3201  GGTGAAAGAC GATGGACAAC TGTTTCATAT AGATTTTGGA CACTTTTTGG  3250
3251  ATCACAAGAA GAAAAAATTT GGTTATAAAC GAGAACGTGT GCCATTTGTT  3300
3301  TTGACACAGG ATTTCTTAAT AGTGATTAGT AAAGGAGCCC AAGAATGCAC  3350
3351  AAAGACAAGA GAATTTGAGA GGTTTCAGGA GATGTGTTAC AAGGCTTATC  3400
3401  TAGCTATTCG ACAGCATGCC AATCTCTTCA TAAATCTTTT CTCAATGATG  3450
3451  CTTGGCTCTG GAATGCCAGA ACTACAATCT TTTGATGACA TTGCATACAT  3500
3501  TCGAAAGACC CTAGCCTTAG ATAAAACTGA GCAAGAGGCT TTGGAGTATT  3550
3551  TCATGAAACA AATGAATGAT GCACATCATG GTGGCTGGAC AACAAAAATG  3600
3601  GATTGGATCT TCCACACAAT TAAACAGCAT GCATTGAACT GA          3642
                                                (SEQ ID NO:3)
```

PIK3CA FUSIONS

This application is a Division of U.S. application Ser. No. 15/304,656, filed Nov. 1, 2016, which is a National Stage Application of and claims priority under 35 USC § 371 to International Application No.: PCT/US2015/026501, filed Apr. 17, 2015, which claims the benefit of U.S. Provisional No. 61/981,546, filed Apr. 18, 2014, all of which are incorporated herein by reference in their entirety.

This invention relates to PIK3CA gene fusions. The invention farther relates to methods of diagnosing and treating diseases or disorders associated with PIK3CA fusions, such as conditions mediated by PIK3CA activity, or conditions associated with aberrant expression or overexpression of PIK3CA.

Many forms of cancer are caused by genetic lesions that give rise to tumor initiation and growth. Genetic lesions may include chromosomal aberrations, such as translocations, inversions, deletions, copy number changes, gene expression level changes, and somatic and germline mutations. Indeed, the presence of such genomic aberrations is a hallmark feature of many cancers, including, for example, B cell cancer, lung cancer, breast cancer, ovarian cancer, pancreatic cancer, and colon cancer. In some models, cancer represents the phenotypic end-point of multiple genetic lesions that endow cells with a full range of biological properties required for tumorigenesis.

Recent efforts by The Cancer Genome Atlas (TCGA), the International Cancer Genome Consortium (ICGC), and dozens of other large-scale profiling efforts have generated an enormous amount of new sequencing data for dozens of cancer types—this includes whole-genome DNA, whole-exome DNA, and full-transcriptome RNA sequencing. These efforts have led to the identification of new driver genes and fusion genes within multiple cancer types. Fusions, particularly fusions involving kinases, are of particular interest, as such fusions have been shown to be oncogenic, and have been successfully targeted by new therapeutics. For example, anaplastic lymphoma kinase (ALK), one of the receptor tyrosine kinases, is known to become oncogenic when fused with various genes. See, e.g., M. Soda et al, "Identification of the transforming EML4-ALK fusion gene in non-small-cell lung cancer," *Nature* 444:561-566(2007).

A need exists for identifying novel genetic lesions associated with cancer. For example, the preset of fusions involving a kinase in samples collected from more than one source can indicate that the kinase is an oncogenic driver. The identification of such fusions can be an effective approach to diagnosis of cancers and development of compounds, compositions, methods, and assays for evaluating and treating cancer patients.

In one aspect, the invention provides methods for detecting the presence of a PIK3CA gene fusion in a biological sample. The methods include the steps of: (a) obtaining a biological sample from a mammal; and (b) contacting the sample with a reagent that detects a PIK3CA gene fusion, to determine whether a PIK3CA gene fusion is present in the biological sample. In some embodiments, the sample can be from a cancer patient, such as, e.g., a breast, uterine, or prostate cancer patient. The fusion can be, e.g., a TBL1XR1:PIK3CA fusion or an FNDC3B:PIK3CA fusion. In some embodiments, the TBL1XR1:PIK3CA fusion comprises all or a part of the nucleotide sequence (such as, e.g., the fusion junction) set forth in SEQ ID NO:1. In some embodiments, the FNDC3B:PIK3CA fusion comprises all or part of the nucleotide sequence (such as, e.g., the fusion junction) set forth in SEQ ID NO:3.

In another aspect, the invention provides methods of diagnosing a patient of having a disease or disorder associated with aberrant PIK3CA activity or expression, or overexpression of PIK3CA; the methods include: (a) obtaining a biological sample from the patient; and (b) contacting the sample with a reagent that detects a PIK3CA gene fusion to determine whether a PIK3CA gene fusion is present in the biological sample, whereby the detection of the PIK3CA gene fusion indicates the presence of a disorder associated with aberrant PIK3CA expression or activity, or overexpression of PIK3CA. In some embodiments, the biological sample is from a tumor of the patient.

The invention also includes methods of determining a therapeutic regimen for treating a cancer in a human subject; methods of identifying a patient likely to respond to treatment with a PIK3CA inhibitor or a PIK3CA fusion inhibitor; methods of stratifying a patient population by detecting a PIK3CA gene fusion; methods of inhibiting the proliferation of cells containing a PIK3CA fusion; methods of treating a condition characterized by overexpression of PIK3CA; methods of treating a condition characterized by aberrant expression or activity of PIK3CA; and method of a identifying an agent that modulates the activity of a PIK3CA fusion; and methods of monitoring disease burden in a patient having a condition mediated by PIK3CA.

BRIEF DESCRIPTION OF THE FIGURES

FIGS. 1A and 1B show the nucleotide sequence of a TBL1XR1-PIK3CA gene fusion (SEQ ID NO:1) comprising a portion of the TBL1XR1 gene up to and including exon 1 and a portion of the PIK3CA gene starting exon 2. The slash after nucleotide 140 indicates the breakpoint (fusion junction) where the fusion has occurred. The underlined nucleotides are the start codon for PIK3CA transcription.

FIG. 2 shows the amino acid sequence for wild type PIK3CA (SEQ ID NO:2).

FIGS. 3A and 3B show the nucleotide sequence of an FNDC3B-PIK3CA gene fusion (SEQ ID NO:3) comprising a portion of the FNDC3B gene up to and including exon 3 and a portion of the PIK3CA gene starting exon 2. The slash after nucleotide 359 indicates the breakpoint (fusion junction) where the fusion has occurred. The underlined nucleotides 436-438 in the PIK3CA sequence are the start codon for PIK3CA transcription.

EXEMPLARY EMBODIMENTS OF THE INVENTION

The invention is based, at least in part, on the discovery of novel recombination or translocation events in cancer patients that result in at least a fragment of a PIK3CA gene linked to a non-homologous promoter via a recombination or translocation event that may result in aberrant expression (e.g., in a location where the kinase is not typically expressed) or overexpression of at least the kinase domain PIK3CA. Thus, a new patient population is identified, which is characterized by the presence of a PIK3CA fusion. This new patient population suffers from or is susceptible to disorders mediated by aberrant PIX3CA expression or activity, or overexpression of PIK3CA, such as, e.g., a cancer. In another aspect of the invention, a new subtype of cancer is identified, which is characterized by the presence of the PIK3CA fusions described herein. In some embodiments, the new patient population suffers from or is susceptible to a breast cancer, uterine cancer, or prostate cancer characterized by the presence of a PIK3CA fusion. New methods of diagnosing and treating the patient population and the PIK3CA fusion cancer subtype are also provided.

Figure 4A:
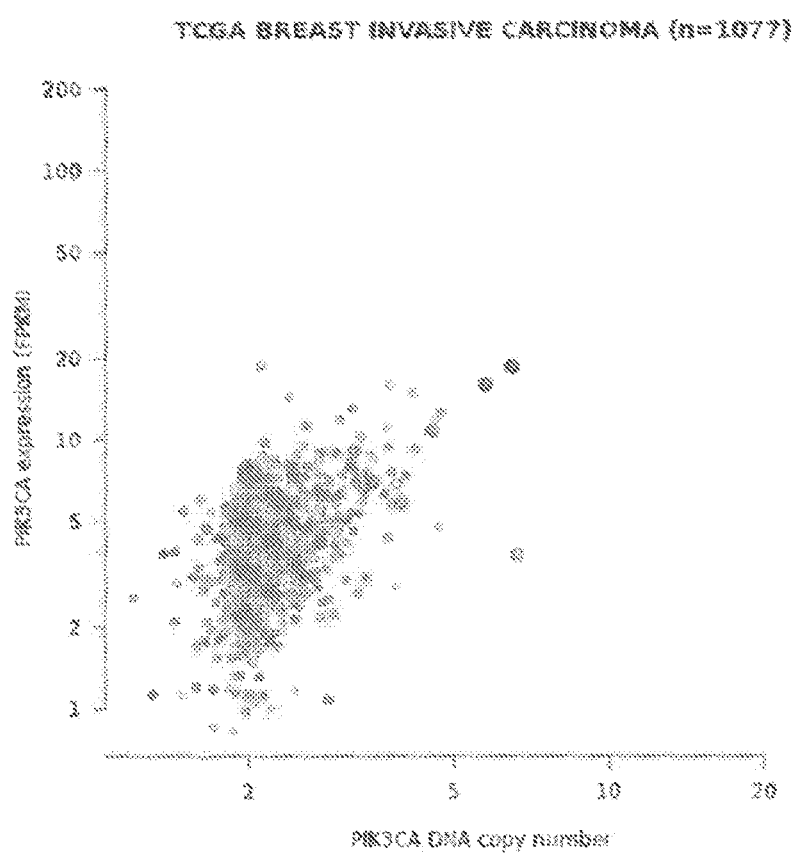
FIG. 4A is a graph showing PIK3CA DNA copy number versus the mRNA expression in breast cancer samples.
Figure 4B:
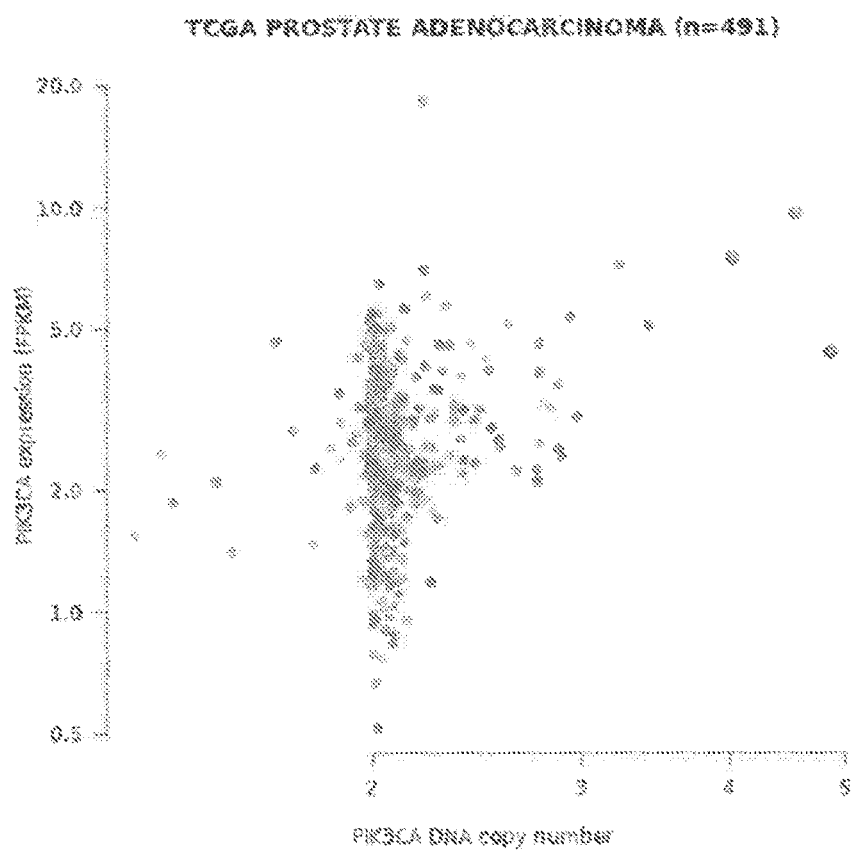
FIG. 4B is a graph showing PIK3CA DNA copy number versus mRNA expression in prostate cancer samples.
Figure 4C:
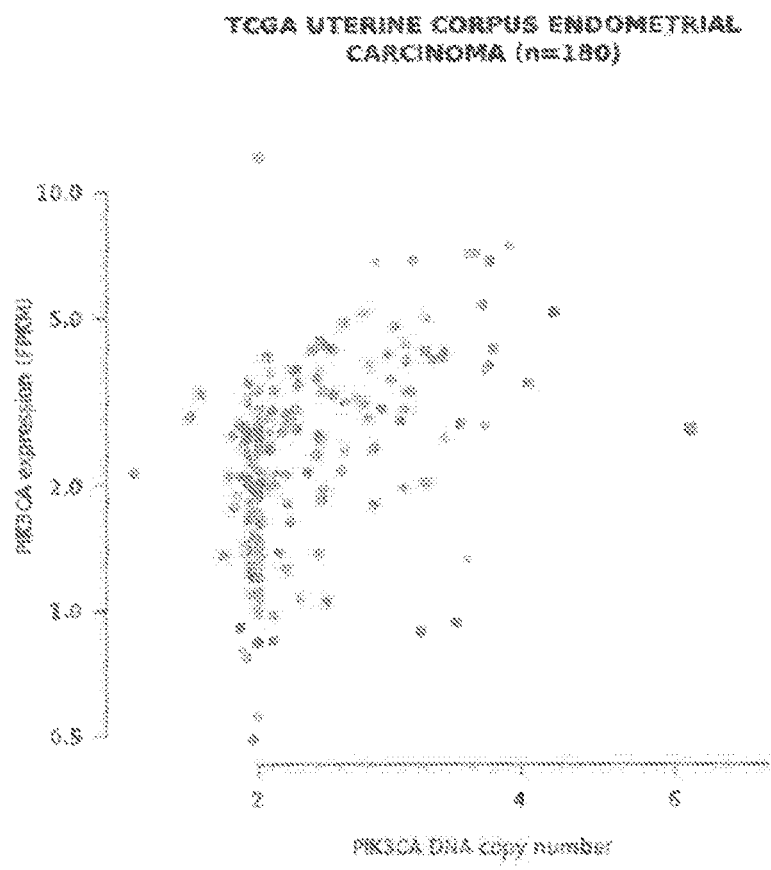
FIG. 4C is a graph showings PIK3CA DNA copy number versus mRNA expression in uterine corpus endometrial carcinoma samples.

The phosphatidylinositol-4,5-bisphosphate 3-kinase, catalytic subunit alpha (PIK3CA), also called p110α protein, is as class IPI 3-kinase catalytic subunit. The human p110α protein is encoded by the PIK3CA gene. PIK3CA is a known oncogene. FIG. 4a shows the DNA copy number versus the mRNA expression (from TCGA) for breast cancer samples; the arrows show the samples in which PIK3CA fusion has occured. The only sample with a higher PIK3CA expression is one with a PIK3CA DNA copy number amplification. FIG. 4b shows the DNA copy number versus the mRNA expression (from TCGA) for prostate cancer samples; the arrow shows the sample in which a PIK3CA fusion has occured. FIG. 4c shows the DNA copy number versus the mRNA expression (from TCGA) for uterine corpus endometrial carcinoma; the arrow shows the sample in which a PIK3CA fusion has occured. The only sample with a higher PIK3CA expression is one with a PIK3CA DNA copy number amplification. This is evidence that PIK3CA fusions such as the ones described here lead to overexpression of PIK3CA.

The term "PIK3CA fusion" is used generically herein, and includes any fusion molecule (e.g., gene, gene product (e.g., cDNA mRNA), and variants thereof) that includes a fragment of the nucleotide sequence for PIK3CA, particularly the coding region for the kinase domain of PIK3CA, and a portion of the nucleotide sequence of another protein (e.g., the promoter and/or the coding region of a non-homologous gene, such that the coding region for the kinase domain of PIK3CA is under control of the non-homologous promoter). Depending on where the fusion point is, the protein that is expressed may comprise the full PIK3CA protein sequence. In some embodiments, the PIK3CA fusion is a TBL1XR1:PIK3CA fusion. In some embodiments, the PIK3CA fusion is an FNDC3B:PIK3CA fusion.

PIK3CA Gene Fusions

PIK3CA gene fusions are generated by a fusion between at least a part of the PIK3CA gene and a part of another gene as a result of a translocation (including inversion) within a chromosome or between chromosomes. As a result of a translocation, the PIK3CA gene may be placed under the transcriptional control of the partner gene promoter, resulting in aberrant PIK3CA expression or activity, or overexpression of PIK3CA. The overexpression can lead to certain cancers, such as breast cancer, uterine cancer (e.g., uterine corpus endometrial cancer), or prostate cancer. As used herein, the 5'-region is upstream of, and the 3'-region is downstream of, a fusion junction or breakpoint in one of the component genes. PIK3CA and the gene that it is fused to may be referred to as "fusion partners." In some exemplary embodiments, the fusion partner is TBL1XR1 (transducin (beta)-like 1 X-linked receptor 1). In other exemplary embodiments, the fusion partner is FNDC3B (fibronectin type III domain containing 3B).

Reference to "all or a portion" or "all or part" of a PIK3CA gene fusion or SEQ ID NO:1 or SEQ NO:3, means that the nucleotide sequence comprises the entire PIK3CA gene fusion nucleotide sequence or a fragment of that sequence that comprises the fusion junction or breakpoint between PIK3CA and its fusion partner (such as, e.g., TBL1XR1 or FNDC3B), The fragment may comprise 7, 8, 9, 10, 12, 14, 16, 18, 20, 21, 22, 23, 24, 25, 26, 27, 2.8, 29, 30, 35, 40, 45, 50, 60, 70, 80, 90, 100, 120, 150, 175, 200, 250, 300, or more nucleotides spatting the fusion junction of the PIK3CA gene fusion.

In one embodiment, a fusion includes all or a portion of the gene TBL1XR1 (e.g., a TBL1XR1 promoter or a functional fragment thereof) and EM exon of the PIK3CA gene (e.g., one or more exons encoding a kinase domain of PIK3CA, or a functional fragment thereof). Such a fusion can be referred to as a TBL1XR1:PIK3CA fusion. In one embodiment, the TBL1XR1:PIK3CA fusion causes the PIK3CA protein to be over-expressed.

In a particular embodiment, the invention provides a TBL1XR1:PIK3CA gene fusion comprising the nucleotide sequence depicted in FIG. 1 (SEQ ID NO:1), or a fragment thereof that includes the fusion junction. SEQ ID NO:1 comprises TBL1XR1 up to exon number 1, in the untranslated region of TBL1XR1, fused to axon number 2, in the untranslated region of the PIK3CA gene. In some embodiments, the TBL1XR1:PIK3CA gene fusion (such as, e.g., SEQ ID NO:1) codes for wild type PIK3CA protein. In some embodiments the TBL1XR1:PIK3CA gene fusion comprises a nucleotide sequence that is at least 85%, at least 90%, at least 95%, at least 97%, or at least 98% identical to all or part of SEQ ID NO:1.

In another embodiment, a fusion includes all or a portion of gene FNDC3B (e.g., FNDC3B promoter or a functional fragment thereof) and an exon of PIK3CA (e.g., one or more axons encoding a PIK3CA kinase domain, or a functional fragment thereof). Such a fusion can be referred to as an FNDC3B:PIK3CA fusion. In one embodiment, the FNDC3B:PIK3CA gene fusion causes the PIK3CA protein to be over-expressed.

In a particular embodiment, the invention provides an FNDC3B:PIK3CA gene fusion comprising the nucleotide sequence in FIG. 3 (SEQ ID NO:3), or a fragment thereof that includes the fusion junction. SEQ ID NO:3 includes the nucleotide sequence of FNDC3B, up to exon number 3, fused to exon number 2 in the untranslated region of PIK3CA. In some embodiments, the FNDC3B:PIK3CA gene fusion (such as, e.g., SEQ ID NO:3) codes for wild type PIK3CA protein. In some embodiments the FNDC:PIK3C.A. gene fusion comprises a nucleotide sequence that is at least 85%, at least 90%, at least 95%, at least 97%, or at least 98% identical to all or part of SEQ ID NO:3.

The nucleic acid sequences of PIK3CA gene fusions may be used as probes, primers, or bait to identify nucleotides from a biological sample that include, flank, or hybridize to PIK3CA fusions, such as, e.g., TBL1XR1:PIK3CA (for example, all or part of SEQ ID NO: 1) or FNDC3B:PIK3CA (for example, all or part of SEQ ID NO:3), at e.g., the fusion junctions. In certain embodiments, the probe, primer, or bait molecule is an oligonucleotide that allows capture, detection, and/or isolation of a PIK3CA gene fusion from a biological sample. In certain embodiments, the probes or primers derived from the nucleic acid sequences of PIK3CA gene fusions (e.g., from the fusion junctions) may be used, for example, for polymerase chain reaction (PCR) amplification. The oligonucleotide can comprise a nucleotide sequence substantially complementary to a fragment of the PIK3CA gene fusion nucleic acid molecules described herein. The sequence identity between the nucleic acid fragment, e.g., the oligonucleotide and the target PIK3CA gene fusion sequence, need not be exact, so long as the sequences are sufficiently complementary to allow the capture, detection or isolation of the target sequence. In one embodiment, the nucleic acid fragment is a probe or primer that includes an oligonucleotide between about 5 and 25, e.g., between 10 and 20, or 10 and 15 nucleotides in length that includes the fusion junction of a PIK3CA fusion, such as, e.g., TBL1XR1:PIK3CA (for example, all or part of SEQ ID NO: 1) or FNDC3B:PIK3CA (for example, all or part of SEQ ID NO:3). In other embodiments, the nucleic acid fragment is a bait that includes an oligonucleotide between about 100 to 300 nucleotides, 130 and 230 nucleotides, or 150 and 200 nucleotides in length that includes the fusion junction of a PIK3CA fusion, such as, e.g., TBL1XR1: PIK3CA (for example, all or part of SEQ ID NO: 1) or FNDC3B:PIK3CA (for example, all or part of SEQ ID NO:3).

In certain embodiments, the nucleic acid fragments hybridize to a nucleotide sequence that includes a breakpoint or fusion junction, e.g., a breakpoint or fusion junction as identified by a slash ("/") in FIGS. 1 and 3. For example, the nucleic acid fragment can hybridize to a nucleotide sequence that includes the fusion junction between the TBL1XR1 transcript and the PIK3CA transcript (e.g., nucleotides 139-141 of SEQ ID NO:1), or between the FNDC3B transcript and the PIK3CA transcript (e.g., nucleotides 358-360 of SEQ ID NO:3), i.e., a nucleotide sequence that includes all or a portion of SEQ ID NO:1 or 3. Examples of such nucleotide sequence may include a portion of SEQ ID NO:1 comprising nucleotides 136-145, 131-150, 116-165, 91-190, 66-215, or 41-240; or a portion of SEQ ID NO:3 comprising nucleotides 355-364, 350-369, 335-384, 310-409, 285-434, or 260-459.

In other embodiments, the nucleic acid fragment includes a bait that comprises a nucleotide sequence that hybridizes to a PIK3CA gene fusion nucleic acid molecule described herein, and thereby allows the detection, capture, and/or isolation of the nucleic acid molecule. In one embodiment, a bait is suitable for solution phase hybridization. In other embodiments, a bait includes a binding entity or detection entity, e.g., an affinity tag or fluorescent label, that allows detection, capture, and/or separation, e.g., by binding to a binding entity, of a hybrid formed by a bait and a nucleic acid hybridized to the bait.

In exemplary embodiments, the nucleic acid fragments used as bait comprise a nucleotide sequence that includes a fusion junction between the TBL1XR1 transcript and the PIK3CA transcript, e.g., a nucleotide sequence within SEQ ID NO:1 comprising nucleotides 139-141 (such as, e.g., a sequence comprising nucleotides 136-145, 131-150, 116-165, 91-190, 66-215, or 41-240 of SEQ ID NO:1) In other exemplary embodiments, the nucleic acid fragments used as bait comprise a nucleotide sequence that includes a fusion junction between the FNDC3B transcript and the PIK3CA transcript, e.g., a nucleotide sequence within SEQ ID NO:3 comprising nucleotides 358-360 such as, e.g., a sequence comprising nucleotides 355-364, 350-369, 335-384, 310-409, 285-434, or 260-459 of SEQ ID NO:3).

Detection and Diagnostic Methods

In another aspect, the invention provides a method of determining the presence of a PIK3CA gene fusion, such as, e.g., a TBL1XR1:PIK3CA or FNDC3B:PIK3CA fusion as described herein. The presence of a PIK3CA gene fusion can indicate that the mammal providing the biological sample suffers from or is at risk of developing a disorder mediated by aberrant PIK3CA expression or activity, or overexpression of PIK3CA, such as, e.g., a cancer. The presence of a PIK3CA gene fusion may also indicate that the cancer is treatable with a PIK3CA inhibitor (such as, e.g., a kinase inhibitor, or an antibody specific to PIK3CA) or a PIK3CA fusion inhibitor. In some embodiments, the cancer is breast cancer. In some embodiments, the cancer is uterine cancer. In some embodiments, the cancer is prostate cancer. In other embodiments, the cancer is a different cancer associated with aberrant expression or activity of PIK3CA or overexpression of PIK3CA.

The method includes detecting whether a PIK3CA fusion nucleic acid molecule is present in a cell (e.g., a circulating cell or a cancer cell), a tissue (e.g., a tumor), or a sample (e.g., a tumor sample), from a subject. In one embodiment, the sample is a nucleic acid sample. In one embodiment, the nucleic acid sample contains DNA, e.g., genomic DNA or cDNA, or RNA, e.g., mRNA.

The methods of the invention may be employed to detect the presence of a PIK3CA fusion polynucleotide in a biological sample of a mammal. In some embodiments, such method comprises the steps of obtaining a biological sample from the mammal and contacting that sample with at least one reagent that detects a PIK3CA fusion, to determine whether a PIK3CA fusion is present in the biological sample. The sample can be chosen from one or more of sample types: such as, e.g., tissue, e.g., cancerous tissue (e.g., a tissue biopsy), whole blood, serum, plasma, buccal scrape, sputum, saliva, cerebrospinal fluid, urine, stool, circulating tumor cells, circulating nucleic acids, or bone marrow.

In some embodiments, the PIK3CA fusion (such as, e.g., TBL1XR1:PIK3CA or FNDC3B:PIK3CA, as disclosed herein) is detected in a nucleic acid molecule by one or more methods chosen from nucleic acid hybridization assays (e.g., in situ hybridization, comparative genomic hybridization, microarray, Southern blot, northern blot), amplification-based assays (e.g., PCR, PCR-RFLP assay, or real-time PCR), sequencing and genotyping, (e.g. sequence-specific primers, high-performance liquid chromatography, or mass-spectrometric genotyping), and screening analysis (including metaphase cytogenetic analysis by, karyotype methods).

(1) Hybridization Methods

In some embodiments, the reagent hybridizes to a PIK3CA gene fusion, such as, e.g., nucleotides 139-141, 136-145, 131-150, 116-165, 91-190, 66-215, or 41-240 of SEQ ID NO:1. In alternate embodiments, the reagent detects the presence of nucleotides 358-360, 355-364, 350-369, 335-384, 310-409, 285-434, or 260-459 of SEQ ID NO:3.

Hybridization, as described throughout the specification, may be carried out under stringent conditions, e.g., medium or high stringency. See, e.g., J. Sambrook, E. F. Fritsch, and T, Maniatis, *Molecular Cloning: A Laboratory Manual*, Cold Spring Harbor Laboratory Pr; 2nd edition (1989); T. Brown, *Hybridization Analysis of DNA Blots. Current Protocols in Molecular Biology* at 21:2.10.1-2.10.16 (2001). High stringency conditions for hybridization refer to conditions under which Iwo nucleic acids must possess a high degree of homology to each other to hybridize. Examples of highly stringent conditions for hybridization include hybridization in 4×sodium chloride/sodium citrate (SSC), at 65 or 70° C. or hybridization in 4×SSC plus 50% formamide at about 42 or 50° C., followed by at least one, at least two, or at least three washes in 1×SSC, at 65 or 70° C. Another example of highly stringent conditions includes hybridization in 2×SSC; 10×Denhardt solution (Fikoll 400+PEG+ BSA; ratio 1:1:1); 0.1% SDS; 5 mM EDTA; 50 mM $Na_2HPO_4$; 250 µg/ml of herring sperm DNA; 50 µg/ml of tRNA; or 0.25 M of sodium phosphate buffer, pH 7.2; 1 mM EDTA7% SDS at 60° C.; followed by washing 2×SSC, 0.1% SDS at 60° C.

The nucleic acid fragments can be detectably labeled with, e.g., a radiolabel, a fluorescent label, a bioluminescent label, a chemiluminescent label, an enzyme label, a binding pair label (e.g., biotin/streptavidin), or can include an affinity tag or identifier (e.g., an adaptor, barcode or other sequence identifier). Labeled or unlabeled nucleic acids and/or nucleic acid fragments may be used in reagents for detecting, capturing, and/or isolating PIK3CA gene fusions, such as, e.g. TBL1XR1:PIK3CA, (for example, all or part of SEQ ID NO:1) or FNDC3B:PIK3CA (for example, all or part of SEQ ID NO:3) In some embodiments, the labeled reagent can be detected using, e.g., nutoradiography, microscopy (e.g., brightfield, fluorescence, or electron microscopy), enzyme-linked immunosorbent assay (ELISA), or immunohistochemistry.

In one embodiment, the method includes: contacting a nucleic acid sample, e.g., a genomic DNA sample (e.g., it chromosomal sample or a fractionated, enriched or otherwise pro-treated sample) or a gene product (mRNA or cDNA), obtained from the subject, with a nucleic acid fragment, e.g., a probe or primer as described herein (e.g., an exon-specific or a breakpoint-specific probe or primer) under conditions suitable for hybridization, and determining the presence or absence of the PIK3CA gene fusion, such as, e.g., TBL1XR1:PIK3CA or FNDC3B:PIK3CA, as disclosed herein.

In some embodiments, the method comprises performing chromosome in situ hybridization with chromosomal DNA from a biological sample to detect the presence of a PIK3CA gene fusion (such as, e.g., TBL1XR1:PIK3CA or FNDC3B:PIK3CA, as disclosed herein). In some embodiments, the chromosome in situ hybridization comprises the steps of: providing a chromosome (e.g., interphase or metaphase chromosome) preparation (e.g., by attaching the chromosomes to a substrate (e.g., glass)); denaturing the chromosomal DNA (e.g., by exposure to formamide) to separate the double strands of the polynucleotides from each other; exposing the nucleic acid probe to the chromosomes under conditions to allow hybridization of the probe to the target DNA; removing unhybridized or non-specifically hybridized probes by washing; and detecting the hybridization of the probe with the target DNA. In some embodiments, the chromosome in situ hybridization is fluorescence in situ hybridization (FISH). In some embodiments, the probe is labeled directly by a fluorescent label, or indirectly by incorporation of a nucleotide containing a tag or reporter molecule (e.g., biotin, digoxigenin, or hapten) which after hybridization to the target DNA is then bound by fluorescently labeled affinity molecule (e.g., an antibody or streptavidin). In some embodiments, the hybridization of the probe with the target DNA in FISH can be visualized using a fluorescence microscope.

In other embodiments, the method comprises performing Southern blot with DNA polynucleotides from a biological sample to detect the presence of a PIK3CA gene fusion. In some embodiments, the Southern blot comprises the steps of: optionally fragmenting the polynucleotides into smaller sizes by restriction endonucleases; separating the polynucleotides by gel electrophoresis; denaturing the polynucleotides (e.g., by heat or alkali treatment) to separate the double strands of the polynucleotides from each other; transferring the polynucleotides from the gel to a membrane (e.g., a nylon or nitrocellulose membrane); immobilizing the polynucleotides to the membrane (e.g., by UV light or heat); exposing the nucleic acid probe to the polynucleotides under conditions to allow hybridization of the probe to the target DNA; removing unhybridized or non-specifically hybridized probes by washing; and detecting the hybridization of the probe with the target DNA.

(2) Amplification-Based Assays

In certain embodiments, the method of determining the presence of a PIK3CA gene fusion, comprises (a) performing a PCR amplification reaction with polynucleotides from a biological sample, wherein the amplification reaction utilizes a pair of primers which will amplify at least a fragment of the PIK3CA gene fusion, wherein the fragment comprises the fusion junction, wherein the first primer is in sense orientation and the second primer is in antisense orientation; and (b) detecting an amplification product, wherein the presence of the amplification product is indicative of the presence of a PIK3CA fusion polynucleotide in the sample. In specific exemplary embodiments, the PIK3CA gene fusion is TBL1XR1:PIK3CA, such as, e.g., the gene fusion of SEQ ID NO: 1, or a fragment thereof, e.g., a nucleotide sequence comprising nucleotides 139-141, 136-145, 131-150, 116-165, 91-190, 66-215, or 41-240 of SEQ ID NO:1, In other exemplary embodiments, the gene fusion is FNDC3B:PIK3CA, such as, e.g. the gene fusion of SEQ ID NO:3 era fragment thereof, e.g., a nucleotide sequence comprising nucleotides 358-360, 355-364, 350-369, 335-384, 310-409, 285-434, or 260-459 of SEQ ID NO:3.

In some embodiments, step (a) of performing a PCR amplification reaction comprises: (i) providing a reaction mixture comprising the polynucleotides (e.g., DNA or cDNA) from the biological sample, the pair of primers which will amplify at least a fragment of the PIK3CA gene fusion wherein the first primer is complementary to a sequence on the first strand of the polynucleotides and the second primer is complementary to a sequence on the second strand of the polynucleotides, a DNA polymerase, and a plurality of free nucleotides comprising adenine, thymine, cytosine, and guanine (dNTPs); (ii) heating the reaction mixture to a first predetermined temperature for a first predetermined time to separate the double strands of the polynucleotides from each other; (iii) cooling the reaction mixture to a second predetermined temperature for a second predetermined time under conditions to allow the first and second primers to hybridize with their complementary sequences on the first and second strands of the polynucleotides, and to allow the DNA polymerase to extend the primers; and (iv) repeating steps (ii) and (iii) for a predetermined number of cycles (e.g., 10, 15, 20, 25, 30, 40, 45, or 50 cycles).

In some embodiments, the polynucleotides from the biological sample comprise RNA, and the method further comprises performing a RT-PCR amplification reaction with the RNA to synthesize cDNA as the template for subsequent or simultaneous PCR reactions. In some embodiments, the RT-PCR amplification reaction comprises providing a reaction mixture comprising the RNA, a primer which will amplify the RNA (e.g., a sequence-specific primer, a random primer, or oligo(dT)s), a reverse transcriptase, and dNTPs, and heating the reaction mixture to a third predetermined temperature for a third predetermined time under conditions to allow the reverse transcriptase to extend the primer.

(3) Sequencing and Genotyping

Another method for determining the presence of a PIK3CA gene fusion molecule (such as, e.g., TBL1XR1:PIK3CA or FNDC3B:PIK3CA, as disclosed herein) includes: sequencing a portion of the nucleic acid molecule (e.g., sequencing the portion of the nucleic acid molecule that comprises the fusion junction of a PIK3CA gene fusion), thereby determining that the PIK3CA gene fusion is present in the nucleic acid molecule. In some exemplary embodiments, the gene fusion is TBL1XR1:PIK3CA. In other exemplary embodiments, the gene fusion is FNDC3B:PIK3CA. Optionally, the sequence acquired is compared to a reference sequence, or a wild type reference sequence. In one embodiment, the sequence is determined by a next generation sequencing method. In some embodiments, the sequencing is automated and/or high-throughput sequencing. The method can further include acquiring, e.g., directly or indirectly acquiring, a sample, e.g., a tumor or cancer sample, from a patient.

In some embodiments, the sequencing comprises chain terminator sequencing (Sanger sequencing), comprising: providing a reaction mixture comprising a nucleic acid molecule from a biological sample, a primer complementary to a region or the template nucleic acid molecule, a DNA polymerase, a plurality of free nucleotides comprising adenine, thymine, cytosine, and guanine (dNTPs), and at least one chain terminating nucleotide (e.g., at least one dideoxynucleotide (ddNTPs) chosen from ddATP, ddTTP, ddCTP, and ddGTP), wherein the at least one chain terminating nucleotide is present in a low concentration so that chain termination occurs randomly at any one of the positions containing the corresponding base on the DNA strand; annealing the primer to a single strand of the nucleic acid molecule; extending the primer to allow incorporation of the chain terminating nucleotide by the DNA polymerase to produce a series of DNA fragments that are terminated at positions where that particular nucleotide is used; separating the polynucleotides by electrophoresis (e.g., gel or capillary electrophoresis); and determining the nucleotide order of the template nucleic acid molecule based on the positions of chain termination on the DNA fragments. In some embodiments, the sequencing is carried out with four separate base-specific reactions, wherein the primer or the chain terminating nucleotide in each reaction is labeled with a separate fluorescent label. In other embodiments, the sequencing is carried out in a single reaction, wherein the four chain terminating nucleotides mixed in the single reaction are each labeled with a separate fluorescent label.

In some embodiments, the sequencing comprises pyrosequencing (sequencing by synthesis), comprising: (i) providing a reaction mixture comprising a nucleic acid molecule from a biological sample, a primer complementary to a region of the template nucleic acid molecule, a DNA polymerase, a first enzyme capable of converting pyrophosphate into ATP, and a second enzyme capable using ATP to generates a detectable signal (e.g., a chemilumninescent signal, such as light) in an amount that is proportional to the amount of ATP; (ii) annealing the primer to a single strand of the nucleic acid molecule; (iii) adding one of the four free nucleotides (dNTPs) to allow incorporation of the correct, complementary dNTP onto the template by the DNA polymerase and release of pyrophosphate stoichiometrically; (iv) converting the released pyrophosphate to ATP by the first enzyme; (v) generating a detectable signal by the second enzyme using the ATP; (vi) detecting the generated signal and analyzing the amount of signal generated in a pyrogram; (vii) removing the unincorporated nucleotides: and (viii) repeating steps (iii) to (vii). The method allows sequencing of a single strand of DNA, one base pair at a time, and detecting which base was actually added at each step. The solutions of each type of nucleotides are sequentially added and removed from the reaction. Light is produced only when the nucleotide solution complements the first unpaired base of the template. The order of solutions which produce detectable signals allows the determination of the sequence of the template.

In some embodiments, the method of determining the presence of a PIK3CA fusion (such as, e.g., TBL1XR1:PIK3CA or FNDC3PIK3CA, as disclosed herein) comprises analyzing a nucleic acid sample (e.g., DNA, cDNA, or RNA, or an amplification product thereof) by HPLC. The method may comprise: passing a pressurized solution containing the sample through a column filled with a sorbent, wherein the nucleic acid or protein components in the sample interact differently with the sorbent, causing different flow rates for the different components; separating the components as they flow out the column at different flow rates. In some embodiments, the HPLC is chosen from, e.g., reverse-phase HPLC, size exclusion HPLC, ion-exchange HPLC, and bioaffinity HPLC.

In some embodiments, the method of determining, the presence of a PIK3CA fusion (such as, e.g., TBL1XR1:PIK3CA or FNDC3B:PIK3CA, as disclosed herein) comprises analyzing a nucleic acid sample (e.g., DNA, cDNA, or RNA, or an amplification product thereof) by mass spectrometry. The method may comprise: ionizing the components in the sample (e.g., by chemical or electron ionization); accelerating and subjecting the ionized components to an electric or magnetic field; separating the ionized components based on their mass-to-charge ratios; and detecting the separated components by a detector capable of detecting charged particles (e.g., by an electron multiplier).

Detection of a PIK3CA gene fusion in a patient can lead to assignment of the patient to the newly identified patient population that bears the PIK3CA fusion. Because this patient population can suffer from or be susceptible to a disorder associated with an aberrant PIK3CA expression or activity, or overexpression of PIK3CA, detection of the PIK3CA fusion can also lead to diagnosis of such disorder. Thus, a further aspect of the invention provides a method of stratifying a patient population (e.g., assigning a patient, to a group or class) and/or diagnosing a patient, comprising: obtaining a biological sample from the patient, contacting the sample to at least one reagent that detects a PIK3CA gene fusion to determine whether a PIK3CA fusion is present in the biological sample. The detection of a PIK3CA fusion indicates that the patient belongs to the newly identified patient population that bears the PIK3CA fusion, and/or the presence of a disorder associated with aberrant PIK3CA expression or activity, or overexpression of PIK3CA, such as e.g., a cancer (e.g., breast cancer, uterine cancer, or prostate cancer). The detection of a PIK3CA fusion also identifies a new subtype of cancer, which is characterized by the presence of the PIK3CA fusion, such as, e.g., certain cancers (e.g., certain breast cancer, uterine cancer, or prostate cancer). In certain embodiments, the PIK3CA fusion is TBL1XR1:PIK3CA. In some embodiments, the TBL1XR:PIK3CA fusion comprises all or part of the nucleotide sequence (such as, e.g., the fusion junction) set forth in SEQ ID NO: 1. In other embodiments, the PIK3CA fusion is FNDC3B:PIK3CA. In some embodiments, the FNDC3B:PIK3CA fusion comprises all or part of the nucleotide sequence (such as, e.g., the fusion junction) set forth in SEQ NO:3.

In some embodiments, the PIK3CA gene fusion is detected prior to initiating, during, and/or after a treatment of a patient with, e.g., a PIK3CA inhibitor (e.g., a kinase inhibitor, or an antibody specific to PIK3CA) or a PIK3CA fusion inhibitor. In one embodiment, the PIK3CA gene fusion is detected at the time the patient is diagnosed with a cancer. In other embodiment, the PIK3CA fusion is detected at a pre-determined interval, e.g., a first point in time and at least at a subsequent point in time. In certain embodiments, in response to detection of a PIK3CA fusion, such as, e.g., TBL1XR1:PIK3CA, FNDC3B:PIK3CA, the method further includes one or more of:

(1) stratifying a patient population (e.g., assigning a patient, to a group or class);

(2) identifying or selecting the patient as likely or unlikely to respond to a treatment, e.g., PIK3CA inhibitor treatment (e.g., a kinase inhibitor treatment) or a PIK3CA fusion inhibitor treatment as described herein;

(3) selecting a treatment regimen, e.g., administering or not administering a preselected therapeutic agent, such as, e.g., PIK3CA inhibitor or a PIK3CA fusion inhibitor;

(4) prognosticating the time course of the disease in the patient (e.g., evaluating the likelihood of increased or decreased patient survival); or (5) monitoring the effectiveness of treatment (e.g., by detecting a reduction in the level of PIK3CA gene fusion in a patient sample).

In certain embodiments, upon detection of a PIK3CA gene fusion in a patient's biological sample, the patient is identified as likely to respond to a treatment that comprises a PIK3CA inhibitor or a PIK3CA fusion inhibitor. In some embodiments, the PIK3CA fusion detected is a TBL1XR1:PIK3CA fusion. In some embodiments, the TBL1XR1:PIK3CA fusion comprises all or part of the nucleotide sequence (such as, e.g., the fusion junction) set forth in SEQ ID NO:1. In alternate embodiments, the PIK3CA fusion detected is an FNDC3B:PIK3CA fusion. In some embodiments, the FNDC3B:PIK3CA fusion comprises all or part of the nucleotide sequence (such as, e.g., the fusion junction) set forth in SEQ ID NO:3.

A further aspect of the invention provides a method of selecting a treatment option by detecting a PIK3CA fusion. The method comprises obtaining a biological sample from a patient and exposing the sample to at least one reagent that detects a PIK3CA gene fusion to determine whether a PIK3CA fusion is present in the biological sample. The detection of the PIK3CA gene fusion indicates the likelihood of the patient responding to treatment with a PIK3CA inhibitor or a PIK3CA fusion inhibitor. The method may be at or personalized by evaluating the effect of a variety of PIK3CA inhibitors or PIK3CA fusion inhibitors on the biological sample shown to contain a PIK3CA fusion to determine the most appropriate inhibitor to administer. In certain embodiments, the PIK3CA fusion is TBL1XR1:PIK3CA. In some embodiments, the TBL1X1:PIK3CA fusion comprises all or part of the nucleotide sequence (such as, e.g., the fusion junction) set forth in SEQ ID NO:1. In other embodiments, the PIK3CA fusion is FNDC3B:PIK3CA. In some embodiments, the FNDC3B:PIK3CA fusion comprises all or part of the nucleotide sequence (such as, e.g., the fusion junction) set forth in SEQ ID NO:3.

Methods of Treatment

Alternatively, or in combination with the detection and diagnostic methods described herein, the invention provides method for treating the newly identified patient population and the new PIK3CA fusion cancer subtype, which are characterized by the presence of a PIK3CA fusion. The patient population and cancer subtype can be associated with or predict the onset of a condition mediated by aberrant PIK3CA expression or activity, or overexpression of PIK3CA, such as, e.g., a cancer or a tumor harboring a PIK3CA fusion (such as, e.g., breast cancer, uterine cancer, or prostate cancer). The methods comprise administering a therapeutic agent, e.g., a PIK3CA inhibitor or a PIK3CA fusion inhibitor, alone or in combination with e.g., other chemotherapeutic agents or procedures, in an amount sufficient to treat a condition mediated by aberrant PIK3CA expression or activity, or overexpression of PIK3CA by one or more of the following: e.g., impeding growth of a cancer, causing a cancer to shrink by weight or volume, extending the expected survival time of the patient, inhibiting tumor growth, reducing tumor mass, reducing size or number of metastatic lesions, inhibiting the development of new metastatic lesions, prolonging survival, prolonging progression-free survival, prolonging time to progression, and/or enhancing quality of life.

In certain embodiments, the PIK3CA fusions of the invention may be inhibited by a PIK3CA inhibitor or a PIK3C.A. fusion inhibitor. In some embodiments, the therapeutic agent is a PIK3CA inhibitor, such as, e.g., a compound, biological or chemical, which inhibits, directly or indirectly, the expression and/or activity of PIK3CA. For example, the PIK3CA inhibitors may be an antibody (such as, e.g., antibodies specific to PIK3CA) or a small molecule inhibitor. In some embodiments, the inhibitors may act directly on PIK3CA itself, modify the activity of PIK3CA, or inhibit the expression of PIK3CA. In other embodiments, the inhibitors may indirectly inhibit PIK3CA activity by inhibiting the activity of proteins or molecules other than PIK3CA itself. For example, the inhibitors may modulate the activity of regulatory kinases that phosphorylate or dephosphorylate PIK3CA, interfere with binding of ligands, or inhibit the activity of interacting or downstream proteins or molecules. Exemplary small molecule inhibitors include pan-kinase inhibitors with activity against several different kinases (including PIK3CA) or specific kinase inhibitors (i.e., kinase inhibitors specific to PIK3CA). In one embodiment, the PIK3C2G fusion, such as, e.g., TBL1XR1PIK3CA or FNDC3B:PIK3CA, is inhibited by a kinase inhibitor.

In some embodiments, the PIK3CA fusion is inhibited by a PIK3CA fusion inhibitor. In some embodiments, the PIK3CA fusion is inhibited by an agent that inhibits transcription or translation of the fusion, e.g., an RNA inhibitor that recognizes the PIK3CA coding sequence, the binding partner (e.g., TBL1XR1 or FNDC3B), or the binding partner: PIK3CA fusion junction, including but not limited to small interfering RNA (siRNA), double stranded RNA (dsRNA) short-hairpin RNA (shRNA), or any other antisense nucleic acid inhibitor. Examples of PIK3CA fusion inhibitors also include other nucleic acid molecules, for example, ribozymes or triple helix molecules, that hybridize to a nucleic acid encoding a PIK3CA-fusion or a transcription regulatory region, and blocks or reduces expression of the PIK3CA fusion. In some embodiments, the PIK3CA fusion inhibited is selected all or a portion of SEQ ID NO: 1 or SEQ ID NO:3.

As used herein, and unless, otherwise specified, a "therapeutically effective amount" of a compound is an amount sufficient to provide a therapeutic benefit in the treatment or management of a condition mediated by aberrant PIK3CA expression or activity, or overexpression of PIK3CA, such as, delaying or minimizing one or more symptoms associated with a cancer or a tumor harboring a PIK3CA fusion (such as, e.g., TBL1XR1:PIK3CA or FNDC3B:PIK3CA, as disclosed herein). A therapeutically effective amount of a compound means an amount of therapeutic agent, alone or in combination with other therapeutic agents, which provides a therapeutic benefit in the treatment or management of the cancer. The term "therapeutically effective amount" can encompass an amount that improves overall therapy.

reduces or avoids symptoms or causes of the condition mediated by aberrant PIK3CA expression or activity, or overexpression of PIK3CA, or enhances the therapeutic efficacy of another therapeutic agent.

In certain embodiments, the cancer or tumor harboring a PIK3CA fusion is breast cancer. In certain embodiments, the cancer or tumor harboring a PIK3CA fusion is uterine cancer. In other embodiments the cancer or tumor harboring a PIK3CA fusion is prostate cancer.

In some embodiments, the patient to be treated is suffering from breast cancer, and the method for treating the condition comprises administering to the patient a therapeutically effective amount of a PIK3CA inhibitor or a PIK3CA fusion inhibitor. In some embodiments, the patient to be treated is suffering from uterine cancer, and the method for treating the condition comprises administering to the patient a therapeutically effective amount of a compound of a PIK3CA inhibitor or a PIK3CA fusion inhibitor. In some embodiments, the patient to be treated is suffering from prostate cancer, and the method for treating the condition comprises administering to the patient a therapeutically effective amount of a compound of a PIK3CA inhibitor or a PIK3CA fusion inhibitor.

Screening Methods

Therapeutic agents, such as e.g., PIK3CA inhibitors or PIK3CA fusion inhibitors, used in the therapeutic methods of the invention can be evaluated using the screening assays described herein. Thus, the invention provides a method of identifying an agent useful for treating a condition mediated by aberrant PIK3CA expression activity, or overexpression of PIK3CA, such as, e.g., cancer or a tumor harboring a PIK3CA fusion (such as e.g., breast cancer, uterine cancer, or prostate cancer), comprising contacting a cell expressing a PIK3CA gene fusion with a candidate agent and determining whether the expression level of the fusion is decreased or a biological function associated with the fusion is altered. In one embodiment, therapeutic agents can be evaluated in a cell-free system, e.g., a cell lysate or in a reconstituted system. In other embodiments, the therapeutic agents are evaluated in a cell in culture, e.g., a cell expressing a PIK3CA fusion (e.g., a mammalian cell, a tumor cell or cell line, a recombinant cell). In yet other embodiments, the therapeutic agents are evaluated in vivo (a PIK3CA fusion-expressing cell present in a subject, e.g., an animal subject (e.g., an in vivo animal model)).

Exemplary parameters to evaluate in determining the efficacy of a therapeutic agent for treating a condition mediated by aberrant PIK3CA expression or activity, or overexpression of PIK3CA, such as, e.g., a cancer or a tumor harboring a PIK3CA fusion include one or more of:
(i) a change in an activity of a cell containing a PIK3CA fusion (e.g., a tumor cell or a recombinant cell), e.g., a change in proliferation, morphology or tumorigenicity of the cell;
(ii) a change in tumor present in an animal subject, e.g., size, appearance, proliferation, of the tumor;
(iii) a change in the level, e.g., expression level, of a PIK3CA gene fusion; or
(iv) a change in an activity of a signaling pathway involving PIK3CA, e.g., phosphorylation or activity of a interacting or downstream target, or expression level of a target gene.

In some embodiments, the PIK3CA fusion is a TBL1XR1:PIK3CA fusion or an FNDC3B:PIK3CA fusion. In some embodiments, the TBL1XR1:PIK3CA fusion comprises all or past of the nucleotide sequence (such as, e.g., the fusion junction) set forth in SEQ ID NO:1. In some embodiments, the FNDC3B:PIK3CA fusion comprises all or part of the nucleotide sequence (such as, e.g., the fusion junction) set forth in SEQ NO:3.

In other embodiments, a change in an activity of a cell expressing a PIK3CA fusion, such as, e.g., TBL1XR1:PIK3CA, or FNDC3B:PIK3CA, as disclosed herein, (e.g., a mammalian cell, a tumor cell or cell line, a recombinant cell) is detected in a cell in culture. In one embodiment, the cell is a recombinant cell that is modified to express a PIK3CA fusion nucleic acid, e.g., is a recombinant cell transfected with a PIK3CA fusion nucleic acid. The transfected cell can show a change in response to the expressed PIK3CA fusion, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or mote of: proliferation, tumorigenicity, transformed morphology, in the presence of the candidate agent can be indicative of an inhibitor of a PIK3CA fusion. In other embodiments, a change in binding activity or phosphorylation of PIK3CA or its interacting or downstream proteins or molecules as described herein is detected.

In yet other embodiment, a change in a tumor present in an animal subject (e.g., an in vivo animal model) is detected. In one embodiment, a tumor containing animal or a xenograft comprising cells expressing a PIK3CA fusion tumorigenic cells expressing a PIK3CA fusion) is employed. The therapeutic agents can be administered to the animal subject and a change in the tumor is evaluated. In one embodiment, the change in the tailor includes one or more of a tumor growth, tumor size, tumor burden, survival, is evaluated. A decrease in one or more of tumor growth, tumor size, tumor burden, or an increased survival is indicative that the candidate agent is an inhibitor or modulator.

In another aspect of the invention provides a method or assay for screening for agents that modulate (e.g., inhibit) the expression or activity of a PIK3CA fusion as described herein. The method includes contacting e.g., a PIK3CA fusion, or a cell expressing a PIK3CA fusion, with a candidate agent; and detecting a change in a parameter associated with a PIK3CA fusion, e.g., a change in the expression or an activity of the PIK3CA fusion. The method can, optionally, include comparing the treated parameter to a reference value, e.g., a control sample (e.g., comparing a parameter obtained from a sample with the candidate agent to a parameter obtained from a sample without the candidate agent). In one embodiment, if a decrease in expression or activity of the PIK3CA fusion is detected, the candidate agent is identified as an inhibitor. In another embodiment, if an increase in expression or activity of the PIK3CA fusion is detected, the candidate agent is identified as an activator. In certain embodiments, the fusion is a PIK3CA gene fusion, where in the fusion is e.g., a TBL1XR1:PIK3CA fusion or an FNDC3B:PIK3CA fusion.

In one embodiment, the contacting step is detected in a cell-free system, e.g., a cell lysate or in a reconstituted system. In other embodiments, the contacting step is detected in a cell in culture, e.g., a cell expressing a PIK3CA fusion (e.g., a mammalian cell, a tumor cell or cell line, a recombinant cell). In yet other embodiments, the contacting step is detected in a cell in vivo (e.g. PIK3CA expressing cell present in a subject, e.g., an animal subject (e.g., an in vivo animal model)).

Exemplary parameters evaluated in identifying an agent that modulates the activity of a PIK3CA fusion (e.g., a TBL1XR1:PIK3CA, fusion or an FNDC3B:PIK3CA fusion) include one or more of:

(i) a change in an activity of a cell containing a PIK3CA fusion (e.g., a tumor cell or recombinant cell), e.g., a change in proliferation, morphology or tumorigenicity of the cell;

(ii) a change in tumor present in an animal subject, e.g., size, appearance, proliferation, of the tumor; or (iii) a change in the level, e.g., expression level, of a PIK3CA fusion; or (iv) a change in an activity of a signaling pathway involving PIK3CA, e.g., phosphorylation or activity of a interacting or downstream target, or expression level of a target gene.

All publications and patents mentioned herein are hereby incorporated by reference in their entirety as if each individual publication or patent was specifically and individually indicated to be incorporated by reference. To the extent publications and patents or patent applications incorporated by reference contradict the disclosure contained in the specification, the specification will supersede any contradictory material. Unless otherwise required by context, singular terms shall include the plural and plural terms shall include the singular. The use of "or" means "and/or" unless stated otherwise. The use of the term "including," as well as other forms, such as "includes" and "included," is not limiting. All ranges given in the application encompass the endpoints unless stated otherwise.

Those skilled in the art will recognize, or be able to ascertain using no more than routine experimentation, many equivalents to the specific embodiments of the invention described herein. Such equivalents are intended to be encompassed by the following claims.

We claim:

1. A method for detecting in a patient a FNDC3B:PIK3CA gene fusion, said method comprising:
   a) contacting a biological sample from the patient with an oligonucleotide that hybridizes under stringent conditions to the fusion junction of the FNDC3B:PIK3CA gene fusion, and detecting hybridization between the FNDC3B:PIK3CA fusion and the oligonucleotide; or
   b) sequencing or amplifying a portion of a nucleic acid from the patient and detecting the presence of a nucleotide sequence comprising at least the FNDC3B:PIK3CA fusion junction,
   wherein the FNDC3B:PIK3CA fusion to be detected comprises SEQ ID NO: 3 or a portion thereof comprising the fusion junction.

2. The method of claim 1, wherein the patient is suffering from or susceptible to a cancer.

3. The method of claim 2, wherein the cancer is chosen from breast cancer, uterine cancer, and prostate cancer.

4. The method of claim 3, wherein the cancer is breast cancer.

5. The method of claim 3, wherein the cancer is uterine cancer.

6. The method of claim 3, wherein the cancer is prostate cancer.

* * * * *

SEQUENCE LISTING

```
<160> NUMBER OF SEQ ID NOS: 3

<210> SEQ ID NO 1
<211> LENGTH: 3423
<212> TYPE: DNA
<213> ORGANISM: Homo sapiens

<400> SEQUENCE: 1
ggggttataa ttgcctctca ccccccggag gggttatttt gggggtggtt ggaggcggtg      60
gcggcggcgg cgaggagggg aatttccttg tgcctccatt cccgggaggg gggagcggcg     120
ttggaggcca ccgtttccag gtttctgctt tgggacaacc atacatctaa ttccttaaag     180
tagttttata tgtaaaactt gcaaagaatc agaacaatgc ctccacgacc atcatcaggt     240
gaactgtggg gcatccactt gatgccccca agaatcctag tagaatgttt actaccaaat     300
ggaatgatag tgactttaga atgcctccgt gaggctacat taataaccat aaagcatgaa     360
ctatttaaag aagcaagaaa atacccctc catcaacttc ttcaagatga atcttcttac     420
attttcgtaa gtgttactca agaagcagaa agggaagaat tttttgatga aacaagacga     480
ctttgtgacc ttcggctttt tcaaccctt ttaaaagtaa ttgaaccagt aggcaaccgt     540
gaagaaaaga tcctcaatcg agaaattggt tttgctatcg gcatgccagt gtgtgaattt     600
gatatggtta aagatccaga agtacaggac ttccgaagaa atattctgaa cgtttgtaaa     660
gaagctgtgg atcttaggga cctcaattca cctcatagta gagcaatgta tgtctatcct     720
ccaaatgtag aatcttcacc agaattgcca aagcacatat ataataaatt agataaaggg     780
caaataatag tggtgatctg ggtaatagtt tctccaaata atgacaagca gaagtatact     840
ctgaaaatca accatgactg tgtaccagaa caagtaattg ctgaagcaat caggaaaaaa     900
actcgaagta tgttgctatc ctctgaacaa ctaaaactct gtgttttaga atatcagggc     960
aagtatattt taaagtgtg tggatgtgat gaatacttcc tagaaaaata tcctctgagt    1020
cagtataagt atataagaag ctgtataatg cttgggagga tgcccaattt gatgttgatg    1080
gctaaagaaa gcctttattc tcaactgcca atggactgtt ttacaatgcc atcttattcc    1140
agacgcattt ccacagctac accatatatg aatggagaaa catctacaaa atcccttt gg    1200 gttataaata gtgcactcag aataaaaatt ctttgtgcaa cctacgtgaa tgtaaatatt    1260
cgagacattg ataagatcta tgttcgaaca ggtatctacc atggaggaga accttatgt     1320 gacaatgtga acactcaaag agtaccttgt tccaatccca gtggaatga atggctgaat    1380
```

```
tatgatatat acattcctga tcttcctcgt gctgctcgac tttgcctttc catttgctct    1440
gttaaaggcc gaaagggtgc taaagaggaa cactgtccat ggcatgggga aaatataaac    1500
ttgtttgatt acacagacac tctagtatct ggaaaaatgg ctttgaatct ttggccagta    1560
cctcatggat tagaagattt gctgaaccct attggtgtta ctggatcaaa tccaaataaa    1620
gaaactccat gcttagagtt ggagtttgac tggttcagca gtgtggtaaa gttcccagat    1680
atgtcagtga ttgaagagca tgccaattgg tctgtatccc gagaagcagg atttagctat    1740
tcccacgcag gactgagtaa cagactagct agagacaatg aattaaggga aaatgacaaa    1800
gaacagctca aagcaatttc tacacgagat cctctctctg aaatcactga gcaggagaaa    1860
gattttctat ggagtcacag acactattgt gtaactatcc ccgaaattct acccaaattg    1920
cttctgtctg ttaaatgaaa ttctagagat gaagtagccc agatgtattg cttggtaaaa    1980
gattggcctc caatcaaacc tgaacaggct atggaacttc tggactgtaa ttacccagat    2040
cctatggttc gaggttttgc tgttcggtgc ttggaaaaat atttaacaga tgacaaactt    2100
tctcagtatt taattcagct agtacaggtc ctaaaatatg aacaatattt ggataacttg    2160
cttgtgagat ttttactgaa gaaagcattg actaatcaaa ggattgggca cttttttctt    2220
tggcatttaa aatctgagat gcacaataaa acagttagcc agaggtttgg cctgcttttg    2280
gagtcctatt gtcgtgcatg tgggatgtat ttgaagcacc tgaataggca agtcgaggca    2340
atggaaaagc tcattaactt aactgacatt ctcaaacagg agaagaagga tgaaacacaa    2400
aaggtacaga tgaagttttt agttgagcaa atgaggcgac cagatttcat ggatgctcta    2460
cagggctttc tgtctcctct aaaccctgct catcaactag gaaacctcag gcttgaagag    2520
tgtcgaatta tgtcctctgc aaaaaggcca ctgtggttga attgggagaa cccagacatc    2580
atgtcagagt tactgtttca gaacaatgag atcatcttta aaaatgggga tgatttacgg    2640
caagatatgc taacacttca aattattcgt attatggaaa atatctggca aaatcaaggt    2700
cttgatcttc gaatgttacc ttatggttgt ctgtcaatcg gtgactgtgt gggacttatt    2760
gaggtggtgc gaaattctca cactattatg caaattcagt gcaaaggcgg cttgaaaggt    2820
gcactgcagt tcaacagcca cactacatca gtggctca aagacaagaa caaaggagaa    2880
atatatgatg cagccattga cctgtttaca cgttcatgtg ctggatactg tgtagctacc    2940
ttcattttgg gaattggaga tcgtcacaat agtaacatca tggtgaaaga cgatggacaa    3000
ctgtttcata tagattttgg acacttttg gatcacaaga gaaaaaatt tggttataaa    3060
cgagaacgtg tgccatttgt tttgacacag gatttcttaa tagtgattag taaaggagcc    3120
caagaatgca caaagacaag agaatttgag aggtttcagg agatgtgtta caaggcttat    3180
ctagctattc gacagcatgc caatctcttc ataaatcttt tctcaatgat gcttggctct    3240
ggaatgccag aactacaatc ttttgatgac attgcataca ttcgaaagac cctagcctta    3300
gataaaactg agcaagaggc tttggagtat ttcatgaaac aaatgaatga tgcacatcat    3360
ggtggctgga caacaaaaat ggattggatc ttccacacaa ttaaacagca tgcattgaac    3420
tga                                                                 3423
```

<210> SEQ ID NO 2
<211> LENGTH: 1068
<212> TYPE: PRT
<213> ORGANISM: Homo sapiens

<400> SEQUENCE: 2

Met Pro Pro Arg Pro Ser Ser Gly Glu Leu Trp Gly Ile His Leu Met

-continued

```
1               5                   10                  15
Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
            35                  40                  45

Leu Phe Lys Glu Ala Arg Lys Tyr Pro Leu His Gln Leu Leu Gln Asp
            50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                    85                  90                  95

Pro Phe Leu Lys Val Ile Glu Pro Val Gly Asn Arg Glu Glu Lys Ile
                100                 105                 110

Leu Asn Arg Glu Ile Gly Phe Ala Ile Gly Met Pro Val Cys Glu Phe
            115                 120                 125

Asp Met Val Lys Asp Pro Glu Val Gln Asp Phe Arg Arg Asn Ile Leu
            130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                    165                 170                 175

Leu Pro Lys His Ile Tyr Asn Lys Leu Asp Lys Gly Gln Ile Ile Val
                180                 185                 190

Val Ile Trp Val Ile Val Ser Pro Asn Asn Asp Lys Gln Lys Tyr Thr
            195                 200                 205

Leu Lys Ile Asn His Asp Cys Val Pro Glu Gln Val Ile Ala Glu Ala
210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                    245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
            275                 280                 285

Ala Lys Glu Ser Leu Tyr Ser Gln Leu Pro Met Asp Cys Phe Thr Met
            290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                    325                 330                 335

Lys Ile Leu Cys Ala Thr Tyr Val Asn Val Asn Ile Arg Asp Ile Asp
                340                 345                 350

Lys Ile Tyr Val Arg Thr Gly Ile Tyr His Gly Gly Glu Pro Leu Cys
            355                 360                 365

Asp Asn Val Asn Thr Gln Arg Val Pro Cys Ser Asn Pro Arg Trp Asn
            370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                    405                 410                 415

Glu Glu His Cys Pro Leu Ala Trp Gly Asn Ile Asn Leu Phe Asp Tyr
                420                 425                 430
```

```
Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
                500                 505                 510

Leu Ser Asn Arg Leu Ala Arg Asp Asn Glu Leu Arg Glu Asn Asp Lys
            515                 520                 525

Glu Gln Leu Lys Ala Ile Ser Thr Arg Asp Pro Leu Ser Glu Ile Thr
        530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
                580                 585                 590

Ile Lys Pro Glu Gln Ala Met Glu Leu Leu Asp Cys Asn Tyr Pro Asp
            595                 600                 605

Pro Met Val Arg Gly Phe Ala Val Arg Cys Leu Glu Lys Tyr Leu Thr
        610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
        690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845
```

```
Glu Val Val Arg Asn Ser His Thr Ile Met Gln Ile Gln Cys Lys Gly
850                 855                 860
Gly Leu Lys Gly Ala Leu Gln Phe Asn Ser His Thr Leu His Gln Trp
865                 870                 875                 880
Leu Lys Asp Lys Asn Lys Gly Glu Ile Tyr Asp Ala Ala Ile Asp Leu
                    885                 890                 895
Phe Thr Arg Ser Cys Ala Gly Tyr Cys Val Ala Thr Phe Ile Leu Gly
                900                 905                 910
Ile Gly Asp Arg His Asn Ser Asn Ile Met Val Lys Asp Asp Gly Gln
                915                 920                 925
Leu Phe His Ile Asp Phe Gly His Phe Leu Asp His Lys Lys Lys Lys
930                 935                 940
Phe Gly Tyr Lys Arg Glu Arg Val Pro Phe Val Leu Thr Gln Asp Phe
945                 950                 955                 960
Leu Ile Val Ile Ser Lys Gly Ala Gln Glu Cys Thr Lys Thr Arg Glu
                965                 970                 975
Phe Glu Arg Phe Gln Glu Met Cys Tyr Lys Ala Tyr Leu Ala Ile Arg
                980                 985                 990
Gln His Ala Asn Leu Phe Ile Asn Leu Phe Ser Met Met Leu Gly Ser
                995                 1000                1005
Gly Met Pro Glu Leu Gln Ser Phe Asp Asp Ile Ala Tyr Ile Arg
    1010                1015                1020
Lys Thr Leu Ala Leu Asp Lys Thr Glu Gln Glu Ala Leu Glu Tyr
    1025                1030                1035
Phe Met Lys Gln Met Asn Asp Ala His His Gly Gly Trp Thr Thr
    1040                1045                1050
Lys Met Asp Trp Ile Phe His Thr Ile Lys Gln His Ala Leu Asn
    1055                1060                1065

<210> SEQ ID NO 3
<211> LENGTH: 3642
<212> TYPE: DNA
<213> ORGANISM: Homo sapiens

<400> SEQUENCE: 3
gcggcggcgg cggctggagg aggagagcgg cggcggcggg agcagcgaag ggggcggcag      60
ggatcctcca ggctgccggc tgggaaggcg tgggcgaccc ggtgtgtggc gcgcccagag     120
ccccgcgttt cagccctagg gaaggaagcc agttgaggga agttctccat gaatgtacgt     180
cacaatgatg atgaccgacc aaatccctct ggaactgcca ccattgctga acggagaggt     240
agccatgatg ccccacttgg tgaatggaga tgcagctcag caggttattc tcgttcaagt     300
taatccaggt gagactttca caataagagc agaggatgga acacttcagt gcattcaagg     360
tttctgcttt gggacaacca tacatctaat tccttaaagt agttttatat gtaaaacttg     420
caaagaatca gaacaatgcc tccacgacca tcatcaggtg aactgtgggg catccacttg     480
atgcccccaa gaatcctagt agaatgttta ctaccaaatg gaatgatagt gactttagaa     540
tgcctccgtg aggctacatt aataaccata agcatgaac tatttaaaga agcaagaaaa      600
taccccctcc atcaacttct tcaagatgaa tcttcttaca ttttcgtaag tgttactcaa     660
gaagcagaaa gggaagaatt ttttgatgaa acaagacgac tttgtgacct tcggcttttt     720
caaccctttt taaagtaat tgaaccagta ggcaaccgtg aagaaaagat cctcaatcga      780
gaaattggtt ttgctatcgg catgccagtg tgtgaatttg atatggttaa agatccagaa     840
gtacaggact tccgaagaaa tattctgaac gtttgtaaag aagctgtgga tcttagggac    900
```

```
ctcaattcac ctcatagtag agcaatgtat gtctatcctc caaatgtaga atcttcacca      960
gaattgccaa agcacatata taataaatta gataaagggc aaataatagt ggtgatctgg     1020
gtaatagttt ctccaaataa tgacaagcag aagtatactc tgaaaatcaa ccatgactgt     1080
gtaccagaac aagtaattgc tgaagcaatc aggaaaaaaa ctcgaagtat gttgctatcc     1140
tctgaacaac taaaactctg tgttttagaa tatcagggca agtatatttt aaaagtgtgt     1200
ggatgtgatg aatacttcct agaaaaatat cctctgagtc agtataagta tataagaagc     1260
tgtataatgc ttgggaggat gcccaatttg atgttgatgg ctaaagaaag cctttattct     1320
caactgccaa tggactgttt tacaatgcca tcttattcca gacgcatttc cacagctaca     1380
ccatatatga atggagaaac atctacaaaa tccctttggg ttataaatag tgcactcaga     1440
ataaaaattc tttgtgcaac ctacgtgaat gtaaatattc gagacattga taagatctat     1500
gttcgaacag gtatctacca tggaggagaa cccttatgtg acaatgtgaa cactcaaaga     1560
gtaccttgtt ccaatcccag gtggaatgaa tggctgaatt atgatatata cattcctgat     1620
cttcctcgtg ctgctcgact ttgccttttcc atttgctctg ttaaaggccg aaagggtgct     1680
aaagaggaac actgtccatt ggcatgggga aatataaact tgtttgatta cacagacact     1740
ctagtatctg gaaaaatggc tttgaatctt tggccagtac ctcatggatt agaagatttg     1800 ctgaaccta ttggtgttac tggatcaaat ccaaataaag aaactccatg cttagagttg     1860
gagtttgact ggttcagcag tgtggtaaag ttcccagata tgtcagtgat tgaagagcat     1920
gccaattggt ctgtatcccg agaagcagga tttagctatt cccacgcagg actgagtaac     1980
agactagcta gagacaatga attaagggaa aatgacaaag aacagctcaa agcaatttct     2040
acacgagatc ctctctctga aatcactgag caggagaaag attttctatg gagtcacaga     2100
cactattgtg taactatccc cgaaattcta cccaaattgc ttctgtctgt taaatggaat     2160
tctagagatg aagtagccca gatgtattgc ttggtaaaag attggcctcc aatcaaacct     2220
gaacaggcta tggaacttct ggactgtaat tacccagatc ctatggttcg aggttttgct     2280
gttcggtgct tggaaaaata tttaacagat gacaaacttt ctcagtattt aattcagcta     2340
gtacaggtcc taaaatatga acaatatttg gataacttgc ttgtgagatt tttactgaag     2400
aaagcattga ctaatcaaag gattgggcac ttttttcttttt ggcatttaaa atctgagatg     2460
cacaataaaa cagttagcca gaggtttggc ctgcttttgg agtcctattg tcgtgcatgt     2520
gggatgtatt tgaagcacct gaataggcaa gtcgaggcaa tggaaaagct cattaactta     2580
actgacattc tcaaacagga gaagaaggat gaaacacaaa aggtacagat gaagttttta     2640
gttgagcaaa tgaggcgacc agatttcatg gatgctctac agggctttct gtctcctcta     2700
aaccctgctc atcaactagg aaacctcagg cttgaagagt gtcgaattat gtcctctgca     2760
aaaaggccac tgtggttgaa ttgggagaac ccagacatca tgtcagagtt actgtttcag     2820
aacaatgaga tcatctttaa aaatggggat gatttacggc aagatatgct aacacttcaa     2880
attattcgta ttatggaaaa tatctggcaa aatcaaggtc ttgatcttcg aatgttacct     2940
tatggttgtc tgtcaatcgg tgactgtgtg ggacttattg aggtggtgcg aaattctcac     3000
actattatgc aaattcagtg caaggcggc ttgaaggtg cactgcagtt caacagccac     3060
acactacatc agtggctcaa agacaagaac aaaggagaaa tatatgatgc agccattgac     3120
ctgtttacac gttcatgtgc tggatactgt gtagctacct tcattttggg aattggagat     3180
cgtcacacaa ta gtaacatcat ggtgaaagac gatggacaac tgtttcatat agattttgga     3240
```

-continued

```
cacttttgg atcacaagaa gaaaaaattt ggttataaac gagaacgtgt gccatttgtt    3300
ttgacacagg atttcttaat agtgattagt aaaggagccc aagaatgcac aaagacaaga    3360
gaatttgaga ggtttcagga gatgtgttac aaggcttatc tagctattcg acagcatgcc    3420
aatctcttca taaatctttt ctcaatgatg cttggctctg gaatgccaga actacaatct    3480
tttgatgaca ttgcatacat tcgaaagacc ctagccttag ataaaactga gcaagaggct    3540
ttggagtatt tcatgaaaca aatgaatgat gcacatcatg gtggctggac aacaaaaatg    3600
gattggatct tccacacaat taaacagcat gcattgaact ga                      3642
```